United States Patent [19]
Harrison et al.

[11] 4,131,683
[45] Dec. 26, 1978

[54] ω-(1,3-DITHIOLAN-2-IMINO) SUBSTITUTED ACETIC ACIDS

[75] Inventors: Boyd L. Harrison; Joseph E. Dolfini, both of Cincinnati, Ohio

[73] Assignee: Richardson-Merrell Inc., Wilton, Conn.

[21] Appl. No.: 905,278

[22] Filed: May 12, 1978

[51] Int. Cl.$^2$ .................. A61K 31/385; C07D 339/06
[52] U.S. Cl. ................................ 424/277; 260/327 M
[58] Field of Search .................... 424/277; 260/327 M

[56] References Cited

U.S. PATENT DOCUMENTS 3,968,232  7/1976  Siegle et al. .................... 424/277

OTHER PUBLICATIONS

Mayer et al., Chem. Abstracts, vol. 62, 13140e (1965).
Campaigne et al., Quaterly Reports On Sulfur Chemistry, vol. 5, pp. 275-303 (1970).
Breslow et al., Multi-Sulfur and Sulfur and Oxygen 5- and 6-Membered Heterocycles, Part I, pp. 532 to 534 and 538 to 548, Interscience Publishers (1966) NY.
Breslow et al., Multi-Sulfur and Sulfur and Oxygen 5- and 6-Membered Heterocycles, Part II, pp. 1001 to 1002, Interscience Publishers (1966) NY.

*Primary Examiner*—John D. Randolph
*Attorney, Agent, or Firm*—William J. Stein; Eugene O. Retter; George W. Rauchfuss, Jr.

[57] ABSTRACT

ω-(1,3-Dithiolan-2-imino) substituted acetic acids are prepared useful as antibacterial agents, inhibitors of cholesterol and fatty acid synthesis, anti-inflammatory agents and as intermediates for cephalosporin antibiotics.

12 Claims, No Drawings

ω-(1,3-DITHIOLAN-2-IMINO) SUBSTITUTED ACETIC ACIDS

FIELD OF THE INVENTION

This invention relates to novel heterocyclic derivatives of acetic acid and their preparation and to their use as anti-inflammatory agents.

SUMMARY OF THE INVENTION

I have discovered that certain heterocyclic derivatives of acetic acid possess useful antibacterial and anti-inflammatory properties as well as inhibiting cholesterol and fatty acid synthesis. Additionally, these compounds are useful as intermediates for the preparation of certain cephalosporin antibiotics. More particularly, these compounds are ω-(1,3-dithiolan-2-imino) substituted acetic acids having the formula

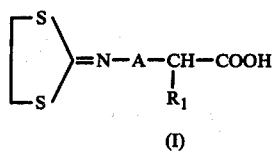

(I)

wherein A is selected from the group consisting of a sigma bond, phenylene and phenylenethio; $R_1$ is selected from the group consisting of hydrogen, lower alkyl having 1 to 4 carbon atoms, phenyl, amino, hydroxy, sulfo and carboxy; and the pharmaceutically acceptable salts thereof.

The present invention discloses a method whereby these compounds may be conveniently prepared in good yield. This reaction may be schematically illustrated as follows:

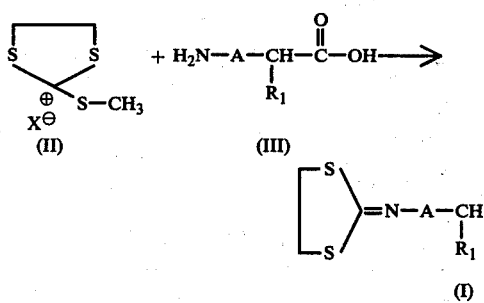

wherein the symbol X is halogen and the remaining symbols have the same meaning as previously described.

Additionally, this invention relates to the use of these compounds as anti-inflammatory agents.

DETAILED DESCRIPTION OF THE INVENTION

As can be seen from general formula (I) above, all of the compounds of the present invention contain the 1,3-dithiolan-2-imino moiety and an acetic acid moiety at the terminal ends of the molecule. For purposes of uniformity of nomenclature, all of the compounds described herein are designated as ω-(1,3-dithiolan-2-imino) substituted acetic acids.

The two variable groups present in general formula I are represented by the symbols A and $R_1$. The symbol A determines the length of the acetic acid side chain. Thus, when A is a sigma bond, the ω-(1,3-dithiolan-2-imino) group is attached directly to the acetic acid side chain. Alternatively, the symbol A may represent the phenylene or phenylenethio groups resulting in ω-(1,3-dithiolan-2-imino) derivatives of phenylacetic acid or of phenylthioacetic acid, respectively.

The symbol $R_1$ defines the various substituents present in the α-position of the acetic acid moiety. Thus, this position can remain unsubstituted as when the symbol $R_1$ is hydrogen, or it may be substituted by a lower alkyl, phenyl, amino, hydroxy, sulfo or carboxy radical. The term lower alkyl is intended to include any monovalent radical derived from an aliphatic hydrocarbon having from 1 to 4 carbon atoms, and includes such groups as the methyl, ethyl, propyl, isopropyl, butyl, isobutyl and t-butyl groups.

When the symbol $R_1$ represents hydrogen, the lower alkyl and phenyl groups, a preferred class of compounds within the broad scope of the present invention is delineated. These compounds possess good anti-inflammatory activity and are particularly useful anti-inflammatory agents.

The pharmaceutically acceptable salts of the compounds of Formula (I) above include the non-toxic, carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and additional amines which have been used to form non-toxic salts with benzylpenicillin. These salts can be prepared using conventional means such as contacting and neutralizing a solution of the carboxylic acid in a polar solvent with a stoichiometric quantity of base. In general, the pharmaceutically acceptable salts are crystalline materials which are more soluble in water and various hydrophilic solvents and which in comparison to their free acid forms generally demonstrate higher melting points and an increased chemical stability.

Illustrative specific free acid compounds encompassed by formula (I) above include:

α-(1,3-dithiolan-2-imino)acetic acid,
α-amino-α-(1,3-dithiolan-2-imino)acetic acid,
α-carboxy-α-(1,3-dithiolan-2-imino)acetic acid,
α-(1,3-dithiolan-2-imino)-α-hydroxyacetic acid,
α-(1,3-dithiolan-2-imino)-α-n-propylacetic acid,
α-(1,3-dithiolan-2-imino)-α-phenylacetic acid,
α-(1,3-dithiolan-2-imino)-α-sulfoacetic acid,
4-(1,3-dithiolan-2-imino)benzeneacetic acid,
α-amino-4-(1,3-dithiolan-2-imino)benzeneacetic acid,
α-carboxy-4-(1,3-dithiolan-2-imino)benzeneacetic acid,
4-(1,3-dithiolan-2-imino)-α-hydroxybenzeneacetic acid,
4-(1,3-dithiolan-2-imino)-α-methylbenzeneacetic acid,
4-(1,3-dithiolan-2-imino)-α-phenylbenzeneacetic acid,
4-(1,3-dithiolan-2-imino)-α-sulfobenzeneacetic acid,
4-(1,3-dithiolan-2-imino)benzenethioacetic acid,
α-amino-4-(1,3-dithiolan-2-imino)benzenethioacetic acid,
α-carboxy-4-(1,3-dithiolan-2-imino)benzenethioacetic acid,
4-(1,3-dithiolan-2-imino)-α-hydroxybenzenethioacetic acid, α-ethyl-4-(1,3-dithiolan-2-imino)benzenethioacetic acid, 4-(1,3-dithiolan-2-imino)-α-phenylbenzenethioacetic acid, and 4-(1,3-dithiolan-2-imino)-α-sulfobenzenethioacetic acid.

The compounds of formula (I) are prepared by condensing an S-alkylated salt of 1,3-dithiolane-2-thione (II) with an ω-amino substituted acetic acid (III) in solution. The S-alkylated salts of 1,3-dithiolane-2-thione are readily prepared by the alkylation of 1,3-dithiolane-2-thione, which is known commercially as ethylenetrithiocarbonate. Thus, for example, the addition of a methyl halide to a solution of 1,3-dithiolane-2-thione at temperatures of from 0°–50° C. for a period of 1 to 24 hours results in the isolation of the corresponding S-methyl halide as a crystalline salt. The S-methyl iodide salt of 1,3-dithiolane-2-thione is the alkylated salt of choice and is prepared by the addition of methyl iodide to a solution of 1,3-dithiolane-2-thione. Preferably, the reaction is conducted via the drop-wise addition of methyl iodide to a nitromethane solution of the 1,3-dithiolane-2-thione at room temperature under an inert atmosphere, as for example, nitrogen or argon.

The various ω-amino substituted acetic acids depicted by general formula III are either well-known compounds that are commercially available or are readily prepared by those skilled in the art using methods described in the literature. Illustrative of these ω-amino substituted acetic acids are glycine, phenylglycine, p-aminophenylglycine, p-aminophenylacetic acid, p-aminophenylthioacetic acid, p-aminomandelic acid, 2-aminomalonic acid and p-aminophenylsulfoacetic acid.

In general, the condensation is conducted by dissolving or suspending the ω-amino substituted acetic acid, or a protected derivative thereof, in a suitable solvent to which the S-alkylated salt of 1,3-dithiolane-2-thione is added at a temperature of from 0°–50° C. for a period of from 1 to 24 hours. Suitable solvents include water, dimethylformamide, diethyl ether, tetrahydrofuran, acetonitrile, dioxane, methanol and aqueous solutions thereof. The solvents of choice are water, dimethylformamide, acetonitrile or dioxane.

Solution of the ω-amino substituted acetic acids and their subsequent condensation with the S-alkylated salt of 1,3-dithiolane-2-thione can be facilitated by the optional addition of a suitable base, such as pyridine, sodium bicarbonate or an alkylamine. Preferably, triethylamine is employed. When the symbol $R_1$ represents either the amino or hydroxy radical, it may also be desirable to employ a suitable protecting group for these radicals, especially when the symbol A is the sigma bond or the phenylenethio radical. Suitable protecting groups include the benzyloxycarbonyl, t-butoxycarbonyl, benzyl, p-methoxybenzyl, trichloroethoxycarbonyl, acetyl and dichloroacetyl derivatives of the α-amino or α-hydroxy substituents. Alternatively, condensation of the α,ω-diamino substituted acetic acids can be conducted at their isoelectric points as per Example 4, thereby permitting condensation to take place at the more nucleophilic ω-amino nitrogen atom.

In general, condensation occurs at a temperature of from 0° to 50° C. over a period of from 1 to 12 hours. Preferably, the condensation reaction is conducted at room temperature in an inert atmosphere, such as nitrogen or argon, with a reaction time of 1–2 hours being all that is required for the reaction to go to completion.

The resulting ω-(1,3-dithiolan-2-imino) substituted acetic acids that are obtained are isolated and purified using standard isolation and purification techniques known to those skilled in the art. Thus, for example, the reaction mixture containing the free acid may be poured into water, and the desired product extracted from the reaction mixture using chloroform, methylene chloride or diethyl ether. The product can then be readily recovered from the organic extracts. Alternatively, the product may precipitate or be caused to precipitate by concentrating the reaction mixture to a small volume and permitting the free acid to crystallize. Recrystallization of the product from such solvents as benzene, ethanol, ethyl acetate, acetone or dimethylformamide generally results in the preparation of white or light colored crystalline material.

Where a base has been employed to facilitate the condensation of the ω-amino substituted acetic acids, the reaction mixture is preferably quenched in water and extracted with an organic solvent to remove any organic by-products that are present. The aqueous layer is acidified and the desired product permitted to crystallize in the form of the free acid using techniques known to those skilled in the art.

The compounds of formula (I) are generally useful as intermediates for the preparation of certain cephalosporin antibiotics. Thus, the ω-(1,3-dithiolan-2-imino) substituted acetic acids (III) can be condensed with various 7-aminocephalosporanic acids to prepare a novel class of cephalosporin antibiotics, as described in copending application Ser. No. 905,215, filed concurrently herewith. Specifically, the compound α-amino-4-(1,3-dithiolan-2-imino)benzeneacetic acid can be condensed with 7-aminodesacetoxycephalosporanic acid to prepare 7-[2-[4-(1,3-dithiolan-2-imino)phenyl]-2-aminoacetylamino]desacetoxycephalosporanic acid, having antimicrobial properties that are comparable to cephalexin against certain gram-positive microorganisms, as for example *Streptococcus pyogenes* and *Staphylococcus aureus*.

The compounds of formula (I) also possess antibacterial properties in and of themselves, effective against certain gram-negative microorganisms as more fully illustrated in Example 7 herein. The compounds of formula (I) also inhibit fatty acid and cholesterol synthesis in vitro. Compounds of this type are useful in the treatment of hyperlipidemia associated with atherosclerosis.

In addition, the compounds of formula (I) possess valuable anti-inflammatory properties useful in the treatment of painful inflammation of the joints as occurs in rheumatoid arthritis as well as in the treatment of various types of non-specific inflammatory or rheumatic conditions affecting the fibromuscular tissues and connective tissues in mammals. The term mammals is intended to include inter alia such mammals as mice, rats, guinea pigs, gerbils, ferrets, dogs, cats, monkeys, cows, horses and humans.

The ω-(1,3-dithiolan-2-imino) substituted acetic acids are administered, as their pharmaceutical salts, in combination with a pharmaceutical carrier in conventional dosage unit forms. Suitable dosage unit forms include oral preparations such as tablets, capsules, powders, granules, oral solutions and suspensions, sublingual and intrabuccal preparations, as well as parenteral dosage unit forms useful for subcutaneous, intramuscular or intravenous administration.

The amount of active ingredient to be administered can vary over a wide range and is dependent upon such factors as the species of animal being treated, its age, health, weight, sex, nature and extent of the particular type of inflammatory disorder treated, and the activity of the particular ω-(1,3-dithiolan-2-imino) substituted acetic acid employed. The total amount of active ingredient to be administered will generally range from about 0.05 to 3.0 grams and preferably from 0.5 to 2.0 grams per day.

The preferred route of administration is via oral administration. Illustrative dosage levels of the active ingredient for oral administration range from 1 to 100 mg per kg of body weight. Preferably, from 10 to 25 mg per kg of the active ingredient are orally administered to humans over a 24 hour period. In those instances where the drug is administered via the parenteral route, corresponding lower dosages are generally employed.

The novel compounds described herein can be administered using various different dosage unit forms, e.g., oral compositions such as tablets, capsules, dragees, lozenges, elixirs, emulsions, liquid solutions or suspensions and various intramuscular, intravenous or intradermal preparations. The preferred dosage unit form is that of either a tablet or a capsule. The amount of active ingredient contained in each dosage unit will, of course, vary according to the activity of the particular ω-(1,3-dithiolan-2-imino) substituted acetic acid employed and the particular dosage unit form employed. In general, a given dosage unit will contain from 10 to 500 mg of the active ingredient in addition to the various pharmaceutical excipients contained therein. Tablets contain 200–400 mg of active ingredient, which are administered t.i.d. or q.i.d., are the preferred dosage unit forms of my invention.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and to prevent adhesion of tablet material to the surfaces of tablet dies and punches. Suitable lubricants include, for example, talc, stearic acid, calcium stearate, magnesium stearate and zinc stearate. Also included within the definition of a pharmaceutical carrier as used herein are disintegrating agents added to assist the breakup and dissolution of tablets following administration, and coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene alcohols, either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5 to about 25% by weight, and preferably from about 1 to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil. For insoluble compounds suspending agents may be added as well as agents to control the viscosity, as for example, magnesium aluminum silicate or carboxymethylcellulose. In addition to these excipients, buffers, preservatives and emulsifying agents may also be added.

The proportion of the active ingredient employed in parenteral dosage unit forms ranges from 0.05 to about 20% by weight, preferably from about 0.1 to about 10% by weight of the total liquid composition, the remaining component or components comprising any of the various pharmaceutical excipients previously mentioned. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol.

The invention described herein is more particularly illustrated in conjunction with the following specific Examples.

EXAMPLE 1

S-Methyl 1,3-dithiolane-2-thione iodide 1,3-Dithiolane-2-thione, (ethylenetrithiocarbonate) 13.6 g, is dissolved in 25 ml of reagent nitromethane and treated at room temperature with 14.2 g of methyl iodide via dropwise addition with stirring under an atmosphere of nitrogen. The reaction mixture is wrapped with foil for light protection and stirring is continued overnight. The crystals that form are filtered, washed with dry benzene and dried in vacuo to yield 20.9 g of brown colored, crystalline S-methyl 1,3-dithiolane-2-thione iodide having a m.pt. of 80°–3° C.

EXAMPLE 2

α-(1,3-Dithiolan-2-imino)-α-phenylacetic acid

D-α-phenylglycine, 1.51 g, is suspended in 30 ml of a 1:1 dioxane-water solution and dissolved by the addition of 15 ml of triethylamine. The solution is cooled in an ice-salt bath, treated with 3.06 g of S-methyl 1,3-dithiolane-2-thione iodide. The reaction mixture is stirred overnight, evaporated to approximately ½ volume in vacuo, filtered and extracted with diethyl ether. The aqueous layer is acidified to pH 2.0 with a solution of 1N HCl and extracted with ethyl acetate. The organic extracts are combined, dried over anhydrous magnesium sulfate and evaporated to dryness in vacuo to yield 0.770 g of an off-white solid having a m.pt. of 67°–82° C. (dec.). An NMR spectrum indicates this material to be the desired D-α-(1,3-dithiolan-2-imino)-α-phenylacetic acid.

Following essentially the same procedure but substituting glycine for the D-α-phenylglycine above results in the formation of α-(1,3-dithiolan-2-imino)acetic acid.

EXAMPLE 3

4-(1,3-Dithiolan-2-imino)benzeneacetic acid

Triethylamine, 15 ml, and 1.51 g of p-aminophenylacetic acid are dissolved at room temperature in 15 ml of sieve-dried dimethylformamide under an inert atmosphere of argon. To this solution is added 3.06 g of S-methyl 1,3-dithiolane-2-thione iodide and the reaction mixture is stirred at room temperature for a period of four hours. The reaction mixture is poured into 100 ml of water, extracted four times with 50 ml portions of methylene chloride followed by two 100 ml extractions with diethyl ether. The aqueous solution is adjusted to pH 1.0 using a concentrated hydrochloric acid solution. The tan solid which precipitates is removed by filtration and dried in vacuo to yield 1.05 g of the desired crude product. The crude material is recrystallized from a hot ethanol-dimethylformamide mixture, filtered and washed with cold ethanol to yield 0.805 g of light tan colored 4-(1,3-dithiolan-2-imino)benzeneacetic acid having a m.pt. of 233°–5° C. (dec.).

Following essentially the same procedure but substituting α-methyl-4-aminobenzeneacetic acid and α-carboxy-4-aminobenzeneacetic acid for the p-aminophenylacetic acid above, results in the preparation of 4-(1,3-dithiolan-2-imino)-α-methylbenzeneacetic acid and 4-(1,3-dithiolan-2-imino)-α-carboxybenzeneacetic acid, respectively.

EXAMPLE 4

α-Amino-4-(1,3-dithiolan-2-imino)benzeneacetic acid

The compound p-aminophenylglycine hydrochloride, 1.0 g, is dissolved in 10 ml of water, adjusted to its isoelectric point (pH approx. 4.8) by means of a 10% solution of sodium hydroxide, and 2.75 g of S-methyl 1,3-dithiolane-2-thione iodide is added in portions thereto. Following the addition of each portion of the dithiolane salt, the pH is readjusted to a pH of 4.8 using a 10% solution of sodium hydroxide. The reacting mixture is stirred overnight, adjusted to a pH of 12.0 using a 10% sodium hydroxide solution, extracted three times with ethyl acetate and once with diethyl ether. The aqueous layer is adjusted to a pH of 5.0 with concentrated hydrochloric acid. The white solid which forms is removed by filtration, washed with ethyl acetate and dried in vacuo to yield 0.640 g of material having a m.pt. of 200°–5° C. An NMR spectrum of this material indicates that the compound α-amino-4-(1,3-dithiolan-2-imino)benzeneacetic acid, is present in approximately 48% yield.

Following essentially the same procedure but substituting p-aminophenylthioglycine hydrochloride for the p-aminophenylglycine hydrochloride above results in the formation of α-amino-4-(1,3-dithiolan-2-imino)benzenethioacetic acid.

EXAMPLE 5

4-(1,3-Dithiolan-2-imino)benzenethioacetic acid

The compound p-aminobenzenethioacetic acid, 7.32 g, is dissolved in 75 ml of sieve-dried dimethylformamide that contains 75 ml of triethylamine. S-methyl 1,3-dithiolane-2-thione iodide, 12.2 g, is added in portions thereto. The reaction mixture is stirred for a period of two hours, and poured into an ice-water mixture. The resulting mixture is extracted several times with methylene chloride followed by an extraction with diethyl ether. The aqueous layer which remains is adjusted to a pH of 3.0 using concentrated hydrochloric acid, whereupon the oil which separates is extracted into ethyl acetate. The ethyl acetate extracts are combined, dried over anhydrous magnesium sulfate and the solvent removed in vacuo. The remaining residue is crystallized from a chloroform-ether solution, recrystallized from a 50:50 chloroform-ethanol solution, and recrystallized once again from a hot ethanol-water solution to yield 3.02 g of 4-(1,3-dithiolan-2-imino)benzenethioacetic acid having a m.pt. of 129°–133° C.

Following essentially the same procedure but substituting α-sulfo-p-aminobenzenethioacetic acid, α-carboxy-p-aminobenzenethioacetic acid and α-methyl-p-aminobenzenethioacetic acid for the p-aminobenzenethioacetic acid above results in the formation of 4-(1,3-dithiolan-2-imino)-α-sulfobenzenethioacetic acid, α-carboxy-4-(1,3-dithiolan-2-imino)benzenethioacetic acid, and 4-(1,3-dithiolan-2-imino)-α-methylbenzenethioacetic acid, respectively.

EXAMPLE 6

4-(1,3-Dithiolan-2-imino)-α-hydroxy-benzeneacetic acid

The compound p-aminomandelic acid, 1.67 g, and 20 ml of triethylamine are dissolved in 20 ml of sieve-dried dimethylformamide and 3.06 g of S-methyl 1,3-dithiolane-2-thione iodide added thereto. The reaction mixture is stirred at room temperature for a period of 2 hours and quenched in 60 ml of an ice cold sodium bicarbonate solution. The resulting mixture is extracted three times with 50 ml portions of methylene chloride and once more with 50 ml of diethyl ether. The aqueous layer is acidified to a pH of 1.0 using concentrated hydrochloric acid, whereupon a white solid precipitates. The precipitate is removed by filtration, washed twice with water, followed by a cold ethanol and ether wash, and air dried to yield 1.46 g of 4-(1,3-dithiolan-2-imino)-α-hydroxy-benzeneacetic acid having a m.pt. of 184°–7° C.

Following essentially the same procedure but substituting α-hydroxy-p-aminobenzenethioacetic acid for the p-aminomandelic acid above results in the formation of 4-(1,3-dithiolan-2-imino)-α-hydroxy-benzenethioacetic acid.

EXAMPLE 7

The following example illustrates the in vitro antibacterial properties of the compounds of this invention.

Trypticase soy broth is inoculated from a stock slant culture of *Proteus mirabilis*, a gram-negative bacterium, and incubated for 24 hours at 37° C. The broth, 0.05 ml is added to 25 ml of melted trypticase soy agar at 45°–50° C., whereupon the seeded agar is poured into a 100 mm square petri dish and allowed to solidify.

Approximately 1 to 3 mg of the test compound is placed on the trypticase soy agar and incubated overnight. The clear zone of inhibition surrounding the test compound is an indication of bacterial inhibition and antibacterial activity. Following essentially the same procedure the compound 4-(1,3-dithiolan-2-imino)benzeneacetic acid exhibits a 7 mm zone of inhibition, whereas under comparable conditions the compound chloramphenicol exhibits a 25 mm zone of inhibition.

EXAMPLE 8

The following example illustrates the in vivo anti-inflammatory activity of the compounds of this invention.

In accordance with the procedure of Winter et al., Proc. Soc. Exp. Biol. Med. 111, 544 (1962), the evaluation of anti-inflammatory agents is determined by the ability of such agents to inhibit the edema produced in the hind paw of the rat by the subplantar injection of a phlogistic agent such as carrageenin. The test compound, 4-(1,3-dithiolan-2-imino)benzeneacetic acid is prepared as a 1% aqueous solution or maintained as a suspension with polyoxyethylene (20) sorbitan monooleate (Tween 80®) and administered at a dosage of 100 mg per kg by oral intubation to groups of five female Sprague-Dawley rats weighing approximately 100 grams. The compound α-methyl-4-(2-methylpropyl)-benzeneacetic acid (ibuprofen), a well-known anti-inflammatory agent, is administered at the same dosage and is used as a positive control. One hour later 0.05 ml of a 1% aqueous solution of carrageenin is administered to the subplantar region of the left hind paw of the rat. Paw edema is measured four hours after the administration of the test compound. Edema is measured as the difference in thickness of paw volume as between the injected and non-injected paw.

In accordance with this procedure, the following data are observed:

|  | Edema (mm) | % Vehicle Control |
|---|---|---|
| Vehicle control (carrageenin only) | 2.55 | 0% |
| Ibuprofen | 1.53 | 60% |
| 4-(1,3-dithiolan-2-imino)-benzeneacetic acid | 1.27 | 50% |

EXAMPLE 9

Preparation of a Tablet Formulation

An illustrative composition for tablets is as follows:

|  | Per Tablet |
|---|---|
| (a) 4-(1,3-dithiolan-2-imino)-benzeneacetic acid | 200 mg |
| (b) Wheat starch | 15 mg |
| (c) Lactose | 83.5 mg |
| (d) Magnesium stearate | 1.5 mg |

The granulation obtained upon mixing lactose, starch and granulated starch paste is dried, screened and mixed with the active ingredient and magnesium stearate. The mixture is compressed into tablets weighing 300 milligrams each.

EXAMPLE 10

Preparation of a Capsule Formulation

An illustrative composition for hard gelatin capsules is as follows:

|  | Per Tablet |
|---|---|
| (a) 4-(1,3-dithiolan-2-imino)-benzeneacetic acid, sodium salt | 200 mg |
| (b) Talc | 35 mg |

The formulation is prepared by passing the dry powders of both (a) and (b) through a fine mesh screen and mixing them well. The powder is then filled into No. 0 hard gelatin capsules at a net fill of 235 mg per capsule. In a similar fashion, a soft gelatin capsule is prepared in which the talc is omitted. The dry 4-(1,3-dithiolan-2-imino)benzeneacetic acid, sodium salt, powder can be filled directly as a granulation, slug or compressed tablet into a rotary dye or plate mold in which the soft gelatin capsule is formed.

EXAMPLE 11

Preparation of Parenteral Formulation

An illustrative composition for a parenteral injection is the following emulsion:

| Each ml Contains | Ingredients | Amount |
|---|---|---|
| 50 mg | 4-(1,3-dithiolan-2-imino)-α-hydroxy-benzeneacetic acid | 1.000 g |
| 100 mg | Polyoxyethylene sorbitan monooleate | 2.000 g |
| 64 mg | Sodium chloride | 0.128 g |
|  | Water for injection, q.s. | 20.000 ml |

The parenteral composition is prepared by dissolving 0.64 g of sodium chloride in 100 ml of water for injection, mixing the polyoxyethylene sorbitan monooleate with the 4-(1,3-dithiolan-2-imino)-α-hydroxybenzeneacetic acid, adding a sufficient solution of the sodium chloride in water to the active ingredient and polyoxyethylene sorbitan monooleate to bring the volume to 20 ml, shaking the mixture, and finally autoclaving the mixture for 20 minutes at 110° C., at 15 p.s.i.g. steam pressure. The composition can be dispensed either in a single ampule for subsequent use in multiple dosage or in groups of 10 and 20 ampules for a single dosage administration.

We claim:

1. An ω-(1,3-dithiolan-2-imino) substituted acetic acid having the formula

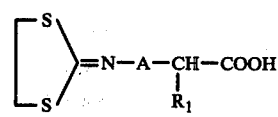

wherein
A is selected from the group consisting of a sigma bond, phenylene and phenylenethio;
$R_1$ is selected from the group consisting of hydrogen, lower alkyl having 1 to 4 carbon atoms, phenyl, amino, hydroxy, sulfo and carboxy; and the pharmaceutically acceptable salts thereof.

2. A compound according to claim 1 wherein X is a sigma bond.

3. A compound according to claim 1 wherein X is phenylene.

4. A compound according to claim 1 wherein $R_1$ is hydrogen, lower alkyl having 1 to 4 carbon atoms and phenyl.

5. A compound of claim 1 which is 4-(1,3-dithiolan-2-imino)benzeneacetic acid.

6. A compound of claim 1 which is 4-(1,3-dithiolan-2-imino)-α-hydroxybenzeneacetic acid.

7. A process for preparing a compound of claim 1 which comprises reacting an ω-amino substituted acetic acid having the formula

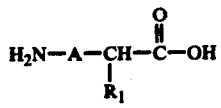

or a pharmaceutically acceptable salt thereof, with S-methyl 1,3-dithiolane-2-thione iodide, in a solvent selected from the group consisting of water, dimethylformamide, diethyl ether, tetrahydrofuran, acetonitrile, dioxane, methanol and aqueous solutions thereof, at a temperature of from 1° to 50° C. for a period of from 1 to 24 hours, and recovering the resulting ω-(1,3-dithiolan-2-imino) substituted acetic acid therefrom.

8. A method of alleviating the symptoms of inflammation in mammals in need thereof comprising the daily administration to said mammals of from 0.05 to 3.0 grams of a compound of claim 1 or a pharmaceutically acceptable salt thereof.

9. A method according to claim 8 wherein from 0.5 to 2.0 grams of compound are administered daily.

10. A method according to claim 8 wherein the compound is 4-(1,3-dithiolan-2-imino)benzeneacetic acid.

11. A therapeutic composition in dosage unit form comprising from 10 to 500 mg of a compound of claim 1 or a pharmaceutically acceptable salt thereof and a pharmaceutically acceptable carrier.

12. A therapeutic composition according to claim 11 wherein the dosage unit is in the form of a tablet.

* * * * *

UNITED STATES PATENT AND TRADEMARK OFFICE
CERTIFICATE OF CORRECTION

PATENT NO. : 4,131,683
DATED : December 26, 1978
INVENTOR(S) : Boyd L. Harrison and Joseph E. Dolfini It is certified that error appears in the above-identified patent and that said Letters Patent are hereby corrected as shown below:

Column 10, lines 54 and 56, the symbol "X" should read "A".

Signed and Sealed this

Eighth Day of January 1980

[SEAL]

Attest:

Attesting Officer

SIDNEY A. DIAMOND
Commissioner of Patents and Trademarks